(12) United States Patent
Clement et al.

(10) Patent No.: US 8,748,493 B2
(45) Date of Patent: Jun. 10, 2014

(54) INHIBITORS OF CATHEPSIN S FOR PREVENTION OR TREATMENT OF OBESITY-ASSOCIATED DISORDERS

(75) Inventors: Karine Clement, Paris (FR); Michele Guerre Millo, Paris (FR); Nadia Naour, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 6 days.

(21) Appl. No.: 13/202,339

(22) PCT Filed: Mar. 22, 2010

(86) PCT No.: PCT/EP2010/053674
§ 371 (c)(1),
(2), (4) Date: Aug. 19, 2011

(87) PCT Pub. No.: WO2010/106187
PCT Pub. Date: Sep. 23, 2010

(65) Prior Publication Data
US 2011/0301242 A1 Dec. 8, 2011

(30) Foreign Application Priority Data

Mar. 20, 2009 (EP) .................................. 09305249
Feb. 4, 2010 (EP) .................................. 10305119

(51) Int. Cl.
*A61K 31/165* (2006.01)
(52) U.S. Cl.
USPC .......................................................... 514/619
(58) Field of Classification Search
USPC .......................................................... 514/619
See application file for complete search history.

(56) References Cited

FOREIGN PATENT DOCUMENTS

WO    WO2008028301    *    3/2008

OTHER PUBLICATIONS

Cywin et al., Bioorganic & Medicinal Chemistry, 2003, 11(5): 733-740.*

* cited by examiner

*Primary Examiner* — Rei-tsang Shiao
(74) *Attorney, Agent, or Firm* — Whitham Curtis Christofferson & Cook, PC

(57) ABSTRACT

The present invention relates to methods (and pharmaceutical compositions) for treating and/or preventing for obesity associated disorders, particularly related to a deregulation of glucose homeostasis, by administrating Cathepsin S inhibitors. The invention also relates to methods for diagnosing insulin resistance and glucose tolerance by measuring Cathepsin S levels in a biological sample obtained from a subject.

1 Claim, 10 Drawing Sheets

Figure 9:
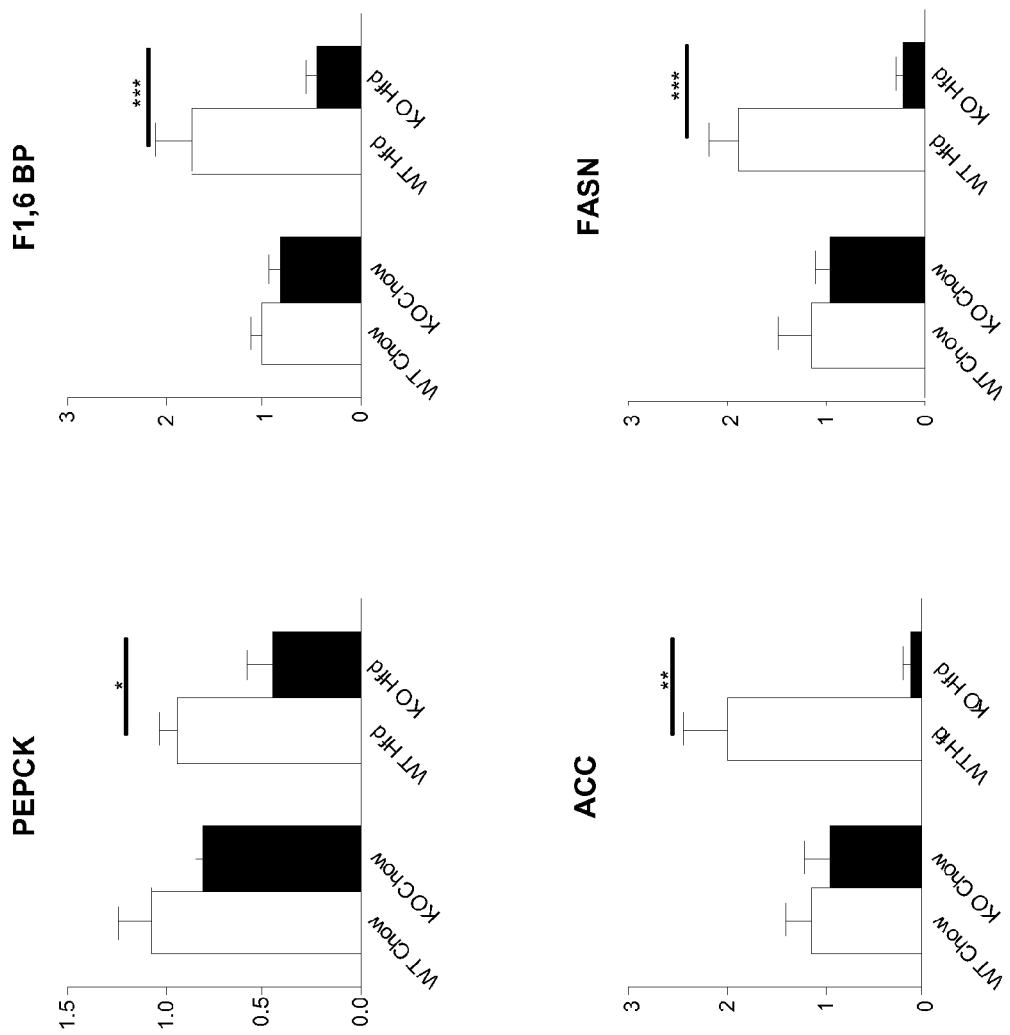

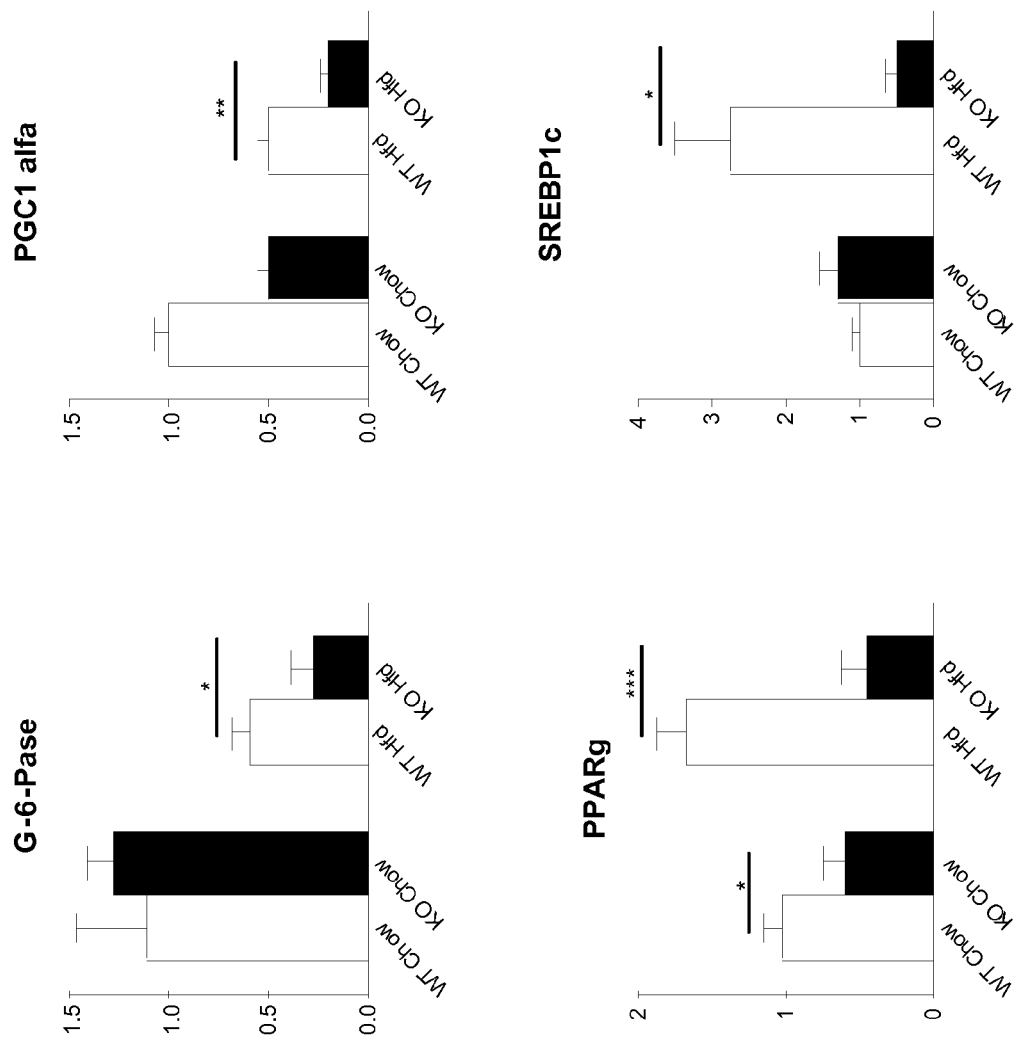
Figure 9 (end)

INHIBITORS OF CATHEPSIN S FOR PREVENTION OR TREATMENT OF OBESITY-ASSOCIATED DISORDERS

FIELD OF THE INVENTION

The present invention relates to methods for the treatment, prevention and diagnosis of obesity associated disorders, particularly related to a deregulation of glucose homeostasis. More particularly the methods of the invention relate to the use of Cathepsin S inhibitors.

BACKGROUND OF THE INVENTION

Obesity is a major nutritional disorder in industrialized and developing countries. The prevalence of obesity and frequently associated type 2 diabetes is rapidly increasing. Back in 1994, it was predicted that there would be 239 million people with diabetes in 2010. In 2007, however, there are already 246 millions diabetic people around the world [Diabetes Atlas 2006; http://www.eatlas.idf.org]. Much of this is driven by the obesity epidemics. WHO (World Health Organization, http://www.who.int) estimates that there are 1.6 billion adults (older than 15) who are overweight and 400 million adults who are obese. This is double of the estimations made in 1995. These numbers increase each year.

Obesity is characterized by accumulation of body fat mass resulting from a positive imbalance between energy intake and energy expenditure. This accumulation of body fat is due to an excess of adipose tissue containing adipocytes, most predominately under the skin, in the abdominal cavity, round the blood vessels, and in mammary gland. A body mass index (BMI=body weight (kg)/height (m)$^2$) above 30 kg/m$^2$ defines obesity.

Obesity is associated with a myriad of complications and an increased risk for type 2 diabetes, dyslipidemia, hypertension, cardiovascular diseases, stroke, hepatic diseases, some cancer, sleep apnea, bone osteoarthritis, infertility, gallstones etc. Particularly, obesity often involves pathologies or disorders associated with deregulation of glucose homeostasis, such as insulin resistance, glucose tolerance and type 2 diabetes.

Type 2 diabetes, also called maturity-onset diabetes mellitus or non-insulin-dependent diabetes mellitus, usually develops rather gradually after the age of 40. However, the number of children and adolescents with type 2 diabetes is increasing at a worrying rate, in parallel with the rise of the incidence of overweight and obesity in the youths.

Type 2 diabetes is a consequence of deregulation of glycemia, which is too elevated. The proper level of blood glucose, or glycemia, is maintained by several hormones. The most important are glucagon, which is a hyperglycemic hormone and insulin, which is the unique hypoglycemic hormone.

The polypeptide hormone insulin acts mainly on muscle, liver, and adipose tissue cells to stimulate the synthesis of glycogen, triglycerides and proteins while inhibiting the breakdown of metabolic fuels, such as triglycerides. In addition, insulin stimulates the uptake of glucose by most cells, with the exception of brain and liver cells. Type 2 diabetic individuals have elevated plasma glucose and insulin levels. This results from resistance to the hypoglycaemic action of insulin in various tissues and organs. The molecular mechanisms of insulin resistance involve post-receptor alteration of signalling in insulin target cells, such as muscle cells. Concomitantly, progressive insulin secretory defect arises due to pancreatic β-cells exhaustion. These dual defects combined lead to reduced glucose tolerance, increased fasting glucose and, eventually, to overt type 2 diabetes (1).

Type 2 diabetes causes various disabling microvascular complications in patients. Besides retinopathy, nephropathy, neuropathy, erectile dysfunction, the disease is also associated with accelerated atherosclerosis and premature cardiovascular morbidity and mortality. Cardiovascular disease accounts for up to 60% of all deaths from diabetes and is the most common complication in Europeans with type 2 diabetes (2); those who are obese in middle age have twice to quadruple risk of being hospitalized for coronary heart disease in old age (3). Indeed, increased incidence of atherosclerosis, myocardial infarction, stroke, and peripheral vascular disease is intricately associated with insulin resistance, which is a major pathophysiologic abnormality in type 2 diabetes. Careful control of glycaemia is needed to reduce the risk of long term complications. This is theoretically achievable with combinations of diet, exercise and weight loss, various oral antidiabetic drugs (metformin, sulfonylureas, glitazones, acarbose), and insulin use for type 2 patients not responding to oral medications (4).

In the field of antidiabetic treatments, however, nearly half of the patients do not achieve their glycaemia target and most therapies (like sulfonylureas and insulin) lead to weight gain (5-7). Thus, there is still a real need for new drugs for preventing and treating this obesity-associated disorder. Preventing or delaying glycaemia deregulation in the early phases of type-2 diabetes could help to reduce the prevalence of this severe and life threatening complication of obesity.

Cathepsins are lysosomal cysteine proteases that belong to the papain superfamily. They are widely distributed and differentially expressed among tissues. These enzymes have a role in processes that involve proteolysis and turnover of specific proteins and tissues. Cathepsins also participate to proenzyme activation and to antigen presentation by MHC class 2 proteins in antigen-presenting cells. The various members of this family are differentially expressed, and some forms of cathepsins are closely associated with monocytes, macrophages, and other cells of the immune system. The secreted forms of several members of this family function in tissue remodelling through degradation of collagen, fibronectin, laminin, elastin, and other structural proteins and are implicated in inflammation associated with immunological response and in metastasis (8). Some cathepsins have been specifically implicated in obesity and related complications. The circulating concentrations of Cathepsin L and S are increased with obesity and type 2 diabetes (9; 10). Cathepsin S is expressed and secreted by human adipose tissue cells, in increasing amounts in response to inflammatory factors (9). Moreover, Cathepsins S, L and K interfere with adipogenesis in vitro and with fat mass accretion in mice (10-12). Cathepsin L has been proposed to be a target for treatment and diagnosis of obesity and diabetes (WO02064613). Cathepsin K and Cathepsin B inhibition are also proposed for the treatment of obesity (CA2561032, WO05097103, WO06076796).

SUMMARY OF THE INVENTION

The invention relates to an inhibitor of Cathepsin S for the treatment and prevention of obesity associated disorders, namely glucose homeostasis. Particularly, the invention relates to an inhibitor of Cathepsin S expression, preferably a selective inhibitor of Cathepsin S expression and to an inhibitor of Cathepsin S activity, preferably a selective inhibitor of Cathepsin S activity.

The invention also relates to pharmaceutical composition for treating obesity and obesity-associated disorder, namely glucose homeostasis, comprising said inhibitor of Cathepsin S.

DETAILED DESCRIPTION OF THE INVENTION

Definitions

The term "glucose homeostasis" is related to any process involved in the maintenance of an internal equilibrium of glucose within the organism. The glucose homeostasis is controlled by many key hormones, which are among others insulin, glucagon, cortisol, and catecholamine.

According to the invention, glucose homeostasis disorders include, but are not limited to, insulin resistance, fasting hyperglycemia and glucose intolerance. As used herein, the term "obesity-associated disorders" refers to disorders which results from obesity or are favoured by obesity. These disorders include, but are not limited to metabolic diseases (type 2 diabetes, hyperglycemia, insulin resistance, hyperinsulinemia, dyslipidemia), cardiovascular diseases, hypertension, pulmonary diseases (asthma, sleep apnoea), hepatic disease (NAFLD, NASH), infertility disorders (OPK), osteoarthritis, gall bladder disease etc. According to the invention, glucose homeostasis disorders are included in the group of obesity-associated disorders.

The term "Cathepsin S" has its general meaning in the art and refers to a secreted cystein protease from the family of Cathepsins (13). The term may include naturally occurring "Cathepsin S" and variants and modified forms thereof. The term may also refer to fusion proteins in which a domain from Cathepsin S that retains the Cathepsin S activity is fused, for example, to another polypeptide (e.g., a polypeptide tag such as are conventional in the art). The Cathepsin S can be from any source, but typically is a mammalian (e.g., human and non-human primate) Cathepsin S, particularly a human Cathepsin S. An exemplary native Cathepsin S amino acid sequence is provided in GenPept database under accession number AAB22005 and an exemplary native nucleotide sequence encoding for Cathepsin S is provided in GenBank database under accession number NM_004079.

The expression "inhibitor of Cathepsin S" should be understood broadly; it encompasses inhibitors of cathepsin S activity and inhibitors of cathepsin S expression. An "inhibitor of expression" refers to a natural or synthetic compound that has a biological effect to inhibit or significantly reduce the expression of a gene. Consequently an "inhibitor of Cathepsin S expression" refers to a natural or synthetic compound that has a biological effect to inhibit or significantly reduce the expression of the gene encoding for the Cathepsin S gene.

Particularly, a "selective inhibitor of cathepsin S expression" refers to such compound which inhibits the Cathepsin S expression more strongly than that of Cathepsins L or K expression in the sense that the inhibitor is at least 10 times, more preferably at least 100 times and most preferably at least 1000 times stronger inhibitor of the Cathepsin S expression.

An "inhibitor of activity" has its general meaning in the art, and refers to a compound (natural or not) which has the capability of reducing or suppressing the activity of a protein. It can be an antibody which binds the activity site of cathepsin S and inhibits its activity.

Particularly, a "selective inhibitor of cathepsin S activity" refers to such compound which inhibits the Cathepsin S activity more strongly than that of Cathepsins L and K activity in the sense that the inhibitor is at least 10 times, more preferably at least 100 times and most preferably at least 1000 times stronger inhibitor of the cathepsin S activity.

As used herein, the term "subject" denotes a mammal, such as a rodent, a feline, a canine, and a primate. Preferably, a subject according to the invention is a human.

An "obese subject" is an otherwise healthy subject with a BMI greater than or equal to 30 kg/m$^2$. A subject with a BMI greater than or equal 27 kg/m$^2$ is considered as overweight.

The term "biological sample" is used herein in its broadest sense. A biological sample is generally obtained from a subject. A sample may be of any biological tissue or fluid in which Cathepsin S may be assayed. Frequently, a sample will be a "clinical sample", i.e., a sample derived from a patient. Such samples include, but are not limited to, body fluids which may or may not contain cells, e.g., blood (e.g., whole blood, serum or plasma), urine, synovial fluid, saliva, and joint fluid; tissue or fine needle biopsy samples, such as from bone or cartilage, and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, cells (or their progeny) isolated from the sample or proteins extracted from the sample. Processing of a biological sample may involve one or more of: filtration, distillation, extraction, concentration, inactivation of interfering components, addition of reagents, and the like. Preferably, biological samples used according to the invention can be obtained from blood (serum, plasma) or from culture media of adipose tissue explants (factors secreted by the adipose tissue).

In its broadest meaning, the term "treating" or "treatment" refers to reversing, alleviating, inhibiting the progress of, or preventing the disorder or condition to which such term applies, or one or more symptoms of such disorder or condition.

In its broadest meaning, the term "preventing" or "prevention" refers to preventing the onset of obesity-associated disorders in an obese subject or subject at risk of obesity.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The term "reference" or "control" refers to a subject that has not shown any glucose homeostasis or weight disorder. Preferably, a normal subject is not on medication affecting glucose homeostasis and has not been diagnosed with any other metabolic disease. In certain embodiments, normal subjects have similar sex, age, and/or body mass index as compared with the subject from which the biological sample to be tested was obtained. A reference sample refers to a sample obtained from such subject and a reference concentration refers to the concentration measured in said biological sample.

Therapeutic Methods and Uses

A first object of the invention relates to methods and compositions (such as pharmaceutical compositions) for treating and/or preventing obesity associated disorders, namely glucose homeostasis.

Obesity associated disorders encompasses, but are not limited to type 2 diabetes, hyperglycemia, insulin resistance, hyperinsulinemia, dyslipidemia, cardiovascular diseases, hypertension, pulmonary diseases, hepatic diseases, infertility disorders, osteoarthritis and gall bladder disease.

In one embodiment, the invention relates to the prevention or treatment of obesity-associated disorders selected from the group consisting of type 2 diabetes, hyperglycemia, insulin resistance and hyperinsulinemia.

In another embodiment, the invention relates to the prevention or treatment of obesity-associated disorders selected from the group consisting of hepatic diseases such as NAFLD and NASH.

In one embodiment, the invention relates to the use of inhibitors of Cathepsin S activity for the treatment of obesity associated disorders. Particularly, the invention relates to the use of selective inhibitors of Cathepsin S activity for the treatment of obesity associated disorders.

In another embodiment, the invention relates to the use of inhibitors of Cathepsin S expression for the treatment of obesity associated disorder. Particularly, the invention relates to the use of selective inhibitors of Cathepsin S expression for the treatment of obesity associated disorders.

Inhibitor of Cathepsin S Activity

In one embodiment, the inhibitor of Cathepsin S activity may be an inhibitor of activity of this Cathepsin, e.g. a small organic molecule. Several molecules have been described as inhibitors of Cathepsin S activity.

According to the invention, inhibitors of Cathepsin S activity that could be used are described in Gauthier JY et al., 2007 (37); particularly, the compound 6 defined by the following formula can be used as a selective inhibitor of Cathepsin S activity:

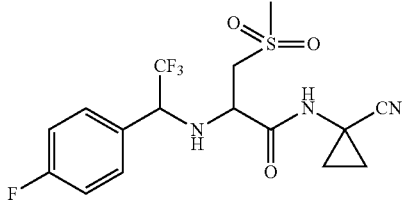 [SMILES: CS(=O)(=O)CC(NC(c1ccc(F)cc1)C(F)(F)F)C(=O)NC1(C#N)CC1]

Other examples of molecules that could be used are: the Paecilopeptin (38) the dipeptide α-keto-β-aldehyde or the 4-Morpholineurea-Leu-HomoPhe-vinylsulphone (LHVS) or an antibody against Cathepsin S described in the patent application WO2007128987. These molecules can also derives from the development of ligand-based and structure-based pharmacophore models for noncovalent and covalent Cathepsin S inhibitors (14) or pyrrolopyrimidine-based inhibitors (15).

In another embodiment the inhibitor of Cathepsin S activity is an antibody or antibody fragment that can partially or completely blocks the Cathepsin S enzymatic activity (i.e. a partial or complete Cathepsin S blocking antibody or antibody fragment).

In particular, the inhibitor of Cathepsin S activity may consist in an antibody directed against the Cathepsin S, in such a way that said antibody blocks the activity of Cathepsin S.

Antibodies directed against the cathepsin S can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against cathepsin S can be prepared and isolated using any technique that provides for the production of antibody molecules by continuous cell lines in culture. Techniques for production and isolation include but are not limited to the hybridoma technique originally described by Kohler and Milstein (16); the human B-cell hybridoma technique (17) and the EBV-hybridoma technique (34). Alternatively, techniques described for the production of single chain antibodies (see, e.g., U.S. Pat. No. 4,946,778) can be adapted to produce anti-cathepsin S, single chain antibodies. Cathepsin S inhibitors useful in practicing the present invention also include anti-cathepsin S fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to cathepsin S.

Humanized anti-cathepsin S antibodies and antibody fragments thereof can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, the inhibitor of cathepsin S activity is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L. (18). The random sequence library is obtainable by combinatorial chemical synthesis of DNA. In this library, each member is a linear oligomer, eventually chemically modified, of a unique sequence. Possible modifications, uses and advantages of this class of molecules have been reviewed in (19). Peptide aptamers consists of a conformationally constrained antibody variable region displayed by a platform protein, such as *E. coli* Thioredoxin A that are selected from combinatorial libraries by two hybrid methods (20).

Inhibitor of Cathepsin S Expression

Another aspect of the invention relates to selective inhibitor of cathepsin S expression. Inhibitors of Cathepsin S expression for use in the present invention may be based on anti-sense oligonucleotide constructs. Anti-sense oligonucleotides, including anti-sense RNA molecules and anti-sense DNA molecules, would act to directly block the translation of cathepsin S mRNA by binding thereto and thus preventing protein translation or increasing mRNA degradation, thus decreasing the level of Cathepsin S, and thus activity, in a cell. For example, antisense oligonucleotides of at least about 15 bases and complementary to unique regions of the mRNA transcript sequence encoding Cathepsin S can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of cathepsin S expression for use in the present invention. Cathepsin S expression can be reduced by contacting a subject or cell with a small double stranded RNA (dsRNA), or a vector or construct causing the production of a small double stranded RNA, such that cathepsin S expression is specifically inhibited (i.e. RNA interference or RNAi). Methods for selecting an appropriate dsRNA or dsRNA-encoding vector are well known in the art for genes whose sequence is known (21-25) U.S. Pat. Nos. 6,573,099 and 6,506,559; and International Patent Publication Nos. WO 01/36646, WO 99/32619, and WO 01/68836). shRNAs (short hairpin RNA) can also function as inhibitors of cathepsin S expression for use in the present invention.

Ribozymes can also function as inhibitors of cathepsin S expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of Cathepsin S mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable.

Both antisense oligonucleotides and ribozymes useful as inhibitors of Cathepsin S expression can be prepared by known methods. These include techniques for chemical synthesis such as, e.g., by solid phase phosphorothioate chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a mean of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs and ribozymes of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and preferably cells expressing Cathepsin S. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in 35.

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms (26). Recombinant AAV are derived from the dependent parvovirus AAV2 (27). The adeno-associated virus type 1 to 12 can be engineered to be replication deficient and is capable of infecting a wide range of cell types and species (26). It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion and most recombinant adenovirus are extrachromosomal.

Other vectors include plasmid vectors. Plasmid vectors have been extensively described in the art and are well known to those of skill in the art. (36). In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript, pSIREN. Other plasmids are well known to those of ordinary skill in the art. Additionally, plasmids may be custom designed using restriction enzymes and ligation reactions to remove and add specific fragments of DNA. Plasmids may be delivered by a variety of parental, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter can be, e.g., a smooth muscle specific promoter, such as a smooth muscle alpha actin promoter, SM22 promoter, cardiac specific promoter, such as cardiac myosin promoter (e.g., a cardiac myosin light chain 2v promoter), troponin T promoter, or BNP promoter. The promoter can also be, e.g., a viral promoter, such as CMV promoter or any synthetic promoters.

The selective inhibitor of cathepsin S activity and/or expression may be administered in the form of a pharmaceutical composition, as defined below.

Preferably, said inhibitor is administered in a therapeutically effective amount. By a "therapeutically effective amount" is meant a sufficient amount of the inhibitor of cathepsin S to treat and/or to prevent obesity associated disorders at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Pharmaceutical Compositions

A further object of the invention relates to a pharmaceutical composition for treating and/or preventing obesity associated disorders, said composition comprising an inhibitor of Cathepsin S expression and/or activity, preferably a selective inhibitor of Cathepsin S expression and/or activity.

In one embodiment, the invention relates to said pharmaceutical composition for treating and/or preventing obesity-associated disorder selected from the group consisting of diabetes, hyperglycemia, insulin resistance and hyperinsulinemia.

In another embodiment, the invention relates to said pharmaceutical composition for treating and/or preventing obesity-associated disorder selected from the group consisting of hepatic diseases such as NAFLD and NASH.

A further object of the invention relates to a pharmaceutical composition for treating and/or preventing obesity associated disorders, namely glucose homeostasis disorders, such as fasting hyperglycemia, glucose intolerance or dyslipidemia, said composition comprising an inhibitor of Cathepsin S expression and/or activity, preferably a selective inhibitor of Cathepsin S expression and/or activity.

The inhibitor(s) of Cathepsin S may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of Cathepsin S of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The inhibitor of Cathepsin S of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Screening Methods

Inhibitors of the invention can be further identified by screening methods described in the state of the art. The screening methods of the invention can be carried out according to known methods.

The screening method may measure the binding of a candidate compound to Cathepsin S, or to cells or membranes bearing Cathepsin S, or a fusion protein thereof by means of a label directly or indirectly associated with the candidate compound. Alternatively, a screening method may involve measuring or, qualitatively or quantitatively, detecting the competition of binding of a candidate compound to the receptor with a labelled competitor (e.g., inhibitor or substrate).

For example, Cathepsin S cDNA may be inserted into an expression vector that contains necessary elements for the transcription and translation of the inserted coding sequence. Following vector/host systems may be utilized such as Baculovirus/Sf9 Insect Cells Retrovirus/Mammalian cell lines like HepB3, LLC-PK1, MDCKII, CHO, HEK293 Expression vector/Mammalian cell lines like HepB3, LLC-PK1, MDCKII, CHO, HEK293. Such vectors may be then used to transfect cells so that said cells express recombinant Cathepsin S at their membrane. It is also possible to use cell lines expressing endogenous Cathepsin S protein such as 3T3-L1 murine fibroblasts and primary human pre-adipocytes, which can be differentiated in mature adipocytes in vitro (11).

Diagnostic Methods

A second object of the invention relates to a method for diagnosing glucose homeostasis disorder, such as insulin resistance or glucose intolerance, in a subject, wherein the concentration of Cathepsin S is measured in a biological sample obtained from said subject and compared with reference sample.

According to the invention, an increased concentration of Cathepsin S in said biological sample than in reference sample is indicative of an insulin resistance and potentially a glucose tolerance. The expression of cathepsin S can be measured at the level of the mRNA or at the level of the protein as follows:

Determination of the expression level of cathepsin S by quantifying mRNAs: total RNAs can be easily extracted from a biological sample according to the invention. The biological sample may be treated prior to its use, e.g. in order to render nucleic acids or proteins available.

Techniques of cell or protein lysis, concentration or dilution of nucleic acids, are known by the skilled person.

Determination of the expression level of cathepsin S can be performed by a variety of techniques. Generally, the expression level as determined is a relative expression level.

More preferably, the determination comprises contacting the sample with selective reagents such as probes, primers or ligands, and thereby detecting the presence, or measuring the amount, of or nucleic acids of interest originally in the sample. Contacting may be performed in any suitable device, such as a plate, microtiter dish, test tube, well, glass, column . . . . In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc.

Level of mRNAs

Methods for determining the quantity of mRNA are well known in the art. For example, the nucleic acid contained in the samples (e.g., cell or tissue prepared from the subject) is first extracted according to standard methods, for example using lytic enzymes or chemical solutions or extracted by nucleic-acid-binding resins following the manufacturer's instructions. The extracted mRNA may be then detected by hybridization (e.g., Northern blot analysis).

Alternatively, the extracted mRNA may be subjected to coupled reverse transcription and amplification, such as reverse transcription and amplification by polymerase chain reaction (RT-PCR), using specific oligonucleotide primers that enable amplification of a region in the nucleic acid of cathepsin S may be used. Quantitative or semiquantitative RT-PCR is preferred. Real-time quantitative or semiquantitative RT-PCR is particularly advantageous. Extracted mRNA may be reverse transcribed and amplified, after which amplified sequences may be detected by hybridization with a suitable probe or by direct sequencing, or any other appropriate method known in the art.

Other methods of Amplification include ligase chain reaction (LCR), transcription mediated amplification (TMA), strand displacement amplification (SDA) and nucleic acid sequence based amplification (NASBA).

In another embodiment, the expression level may be determined by DNA microarray analysis. Such DNA microarray or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of 5 complexes between 20 target nucleic acids that are complementary to probe sequences attached to the microarray surface. The labelled hybridized complexes are then detected and can be quantified or semiquantified.

Labelling may be achieved by various methods, e.g. by using radioactive or fluorescent labelling. Many variants of the microarray hybridization technology are available to the man skilled in the art [for a review see (28)].

Level of Proteins

Determination of the expression level of Cathepsin S by quantifying proteins: other methods exist for determining the expression level of Cathepsin S.

Such methods comprise contacting a biological sample with a binding partner capable of selectively interacting with the Cathepsin S present in the sample. The binding partner is generally an antibody that may be polyclonal or monoclonal, preferably monoclonal.

The presence of the Cathepsin S can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, immunocytochemistry, immunohistochemistry, etc. The reactions generally include revealing labels such as fluorescent, chemiluminescent, radioactive, enzymatic labels or dye molecules, or other methods for detecting the formation of a complex between the antigen and the antibody or antibodies reacted therewith.

More particularly, an ELISA method can be used, wherein the wells of a microtiter plate are coated with a set of antibodies against the proteins to be tested. A biological sample containing or suspected of containing the marker protein is then added to the coated wells.

After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

FIGURES

Figure 1:
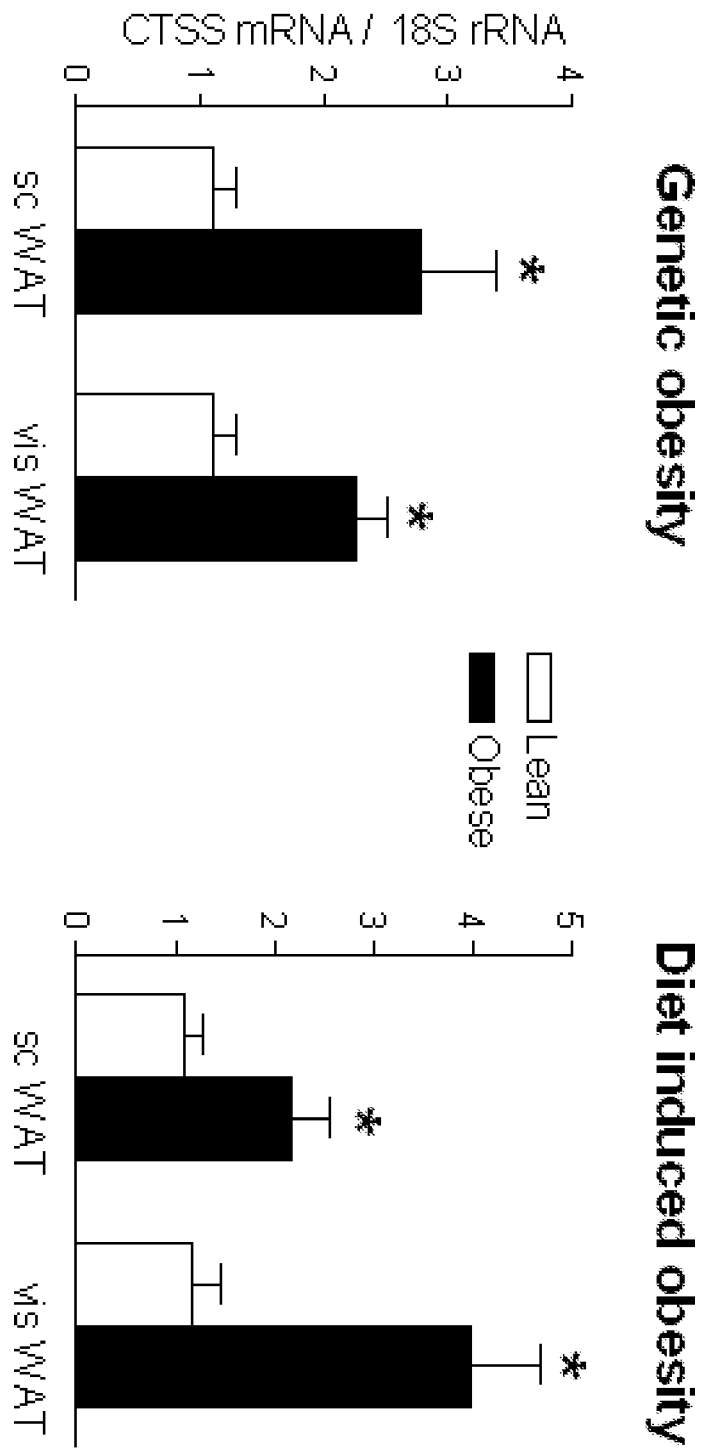

FIG. 1: Cathepsin S gene expression is increased in adipose tissue of genetic or diet-induced rodent models of obesity.

Genetic obesity: Male obese (fa/fa) Zucker rats were compared to their lean (Fa/fa) counterpart (n=8 per genotype). Diet-induced obesity: Male wild type mice were submitted to 12 weeks of a high fat diet and compared to wild-type mice fed a normal chow diet (n=8 per group). CTSS: Cathepsin S; sc WAT: subcutaneous adipose tissue; visc WAT: visceral adipose tissue; * p<0.05 versus lean, FIG. 2: Cathepsin S activity is readily detectable in the spleen of wild type (WT) mice and absent in Cathepsin S deficient mice (CTSS KO). Cathepsin S activity was measured in spleen tissular extracts from 12 mice in each group. * p<0.05 versus WT.

Figure 3:
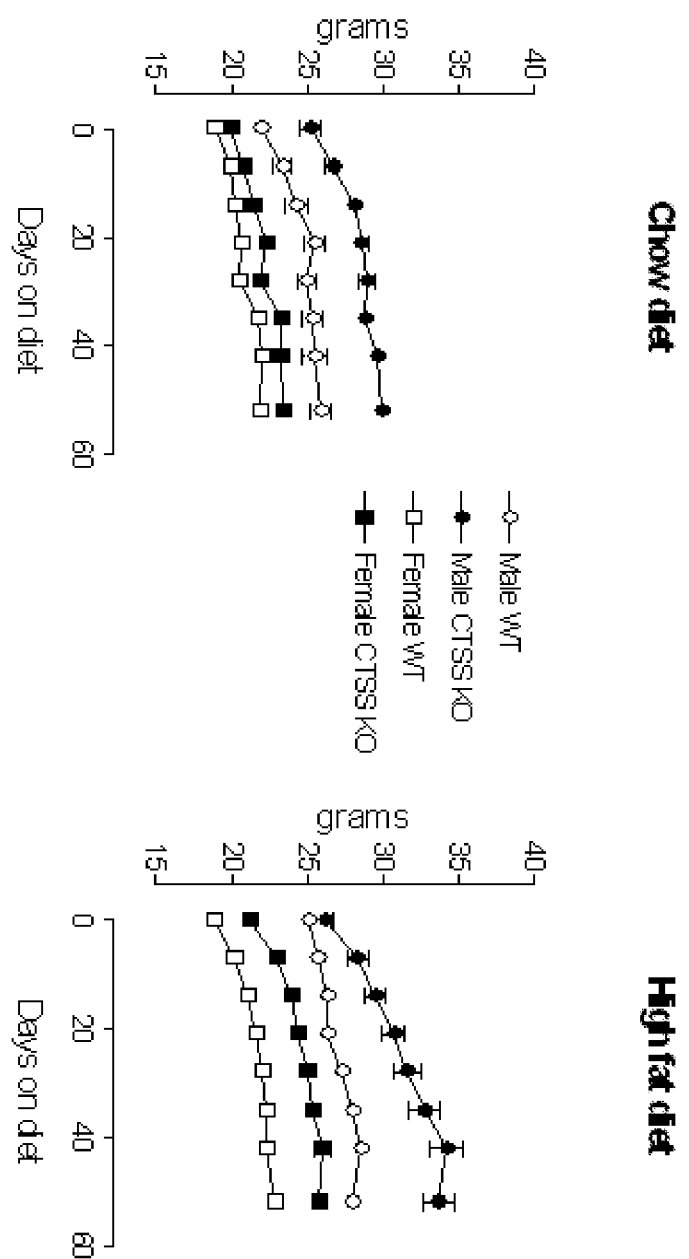

FIG. 3: Body weight is slightly increased in Cathepsin S deficient mice (CTSS KO), as compared to age and gender matched wild type control mice (WT), whatever the diet. Body weight was measured weekly in at least 15 mice per group.

Figure 4:
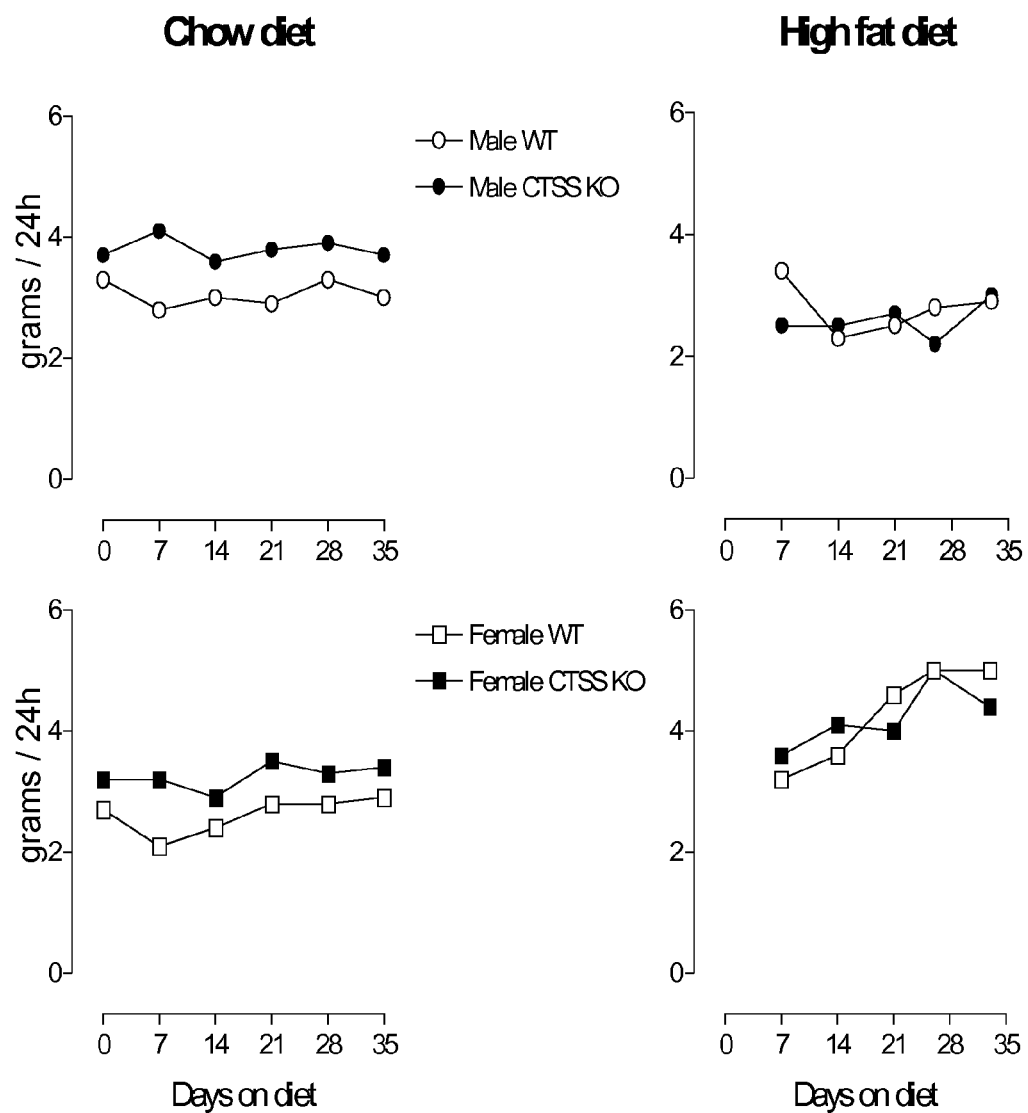

FIG. 4: Food intake is higher in Cathepsin S deficient mice (CTSS KO) than in wild-type mice (WT) under normal chow diet. This phenotype is no longer apparent under high fat diet.

Figure 5:
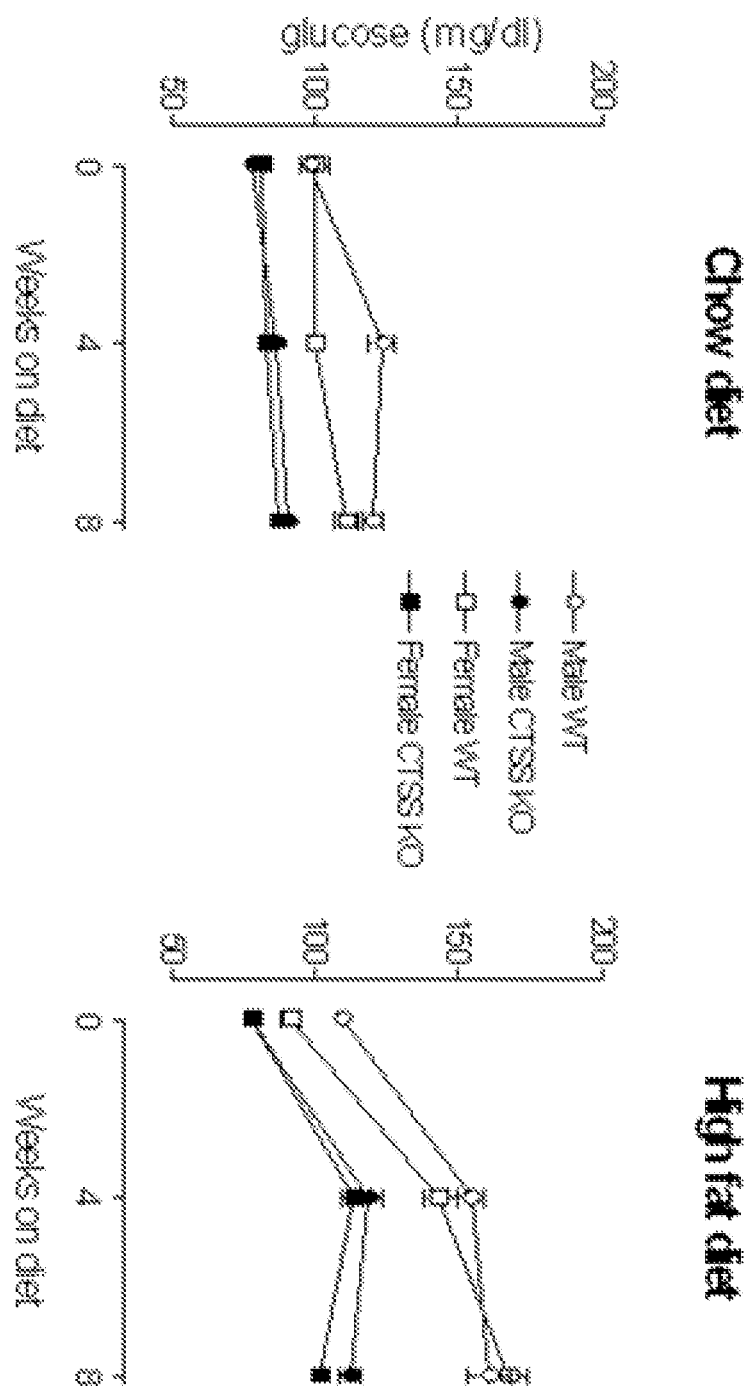

FIG. 5: Fasting blood glucose is consistently lower in Cathepsin S deficient mice (CTSS KO) than in wild-type control mice (WT), for mice of both sexes and whatever the diet. n=10 to 12 per group.

Figure 6:
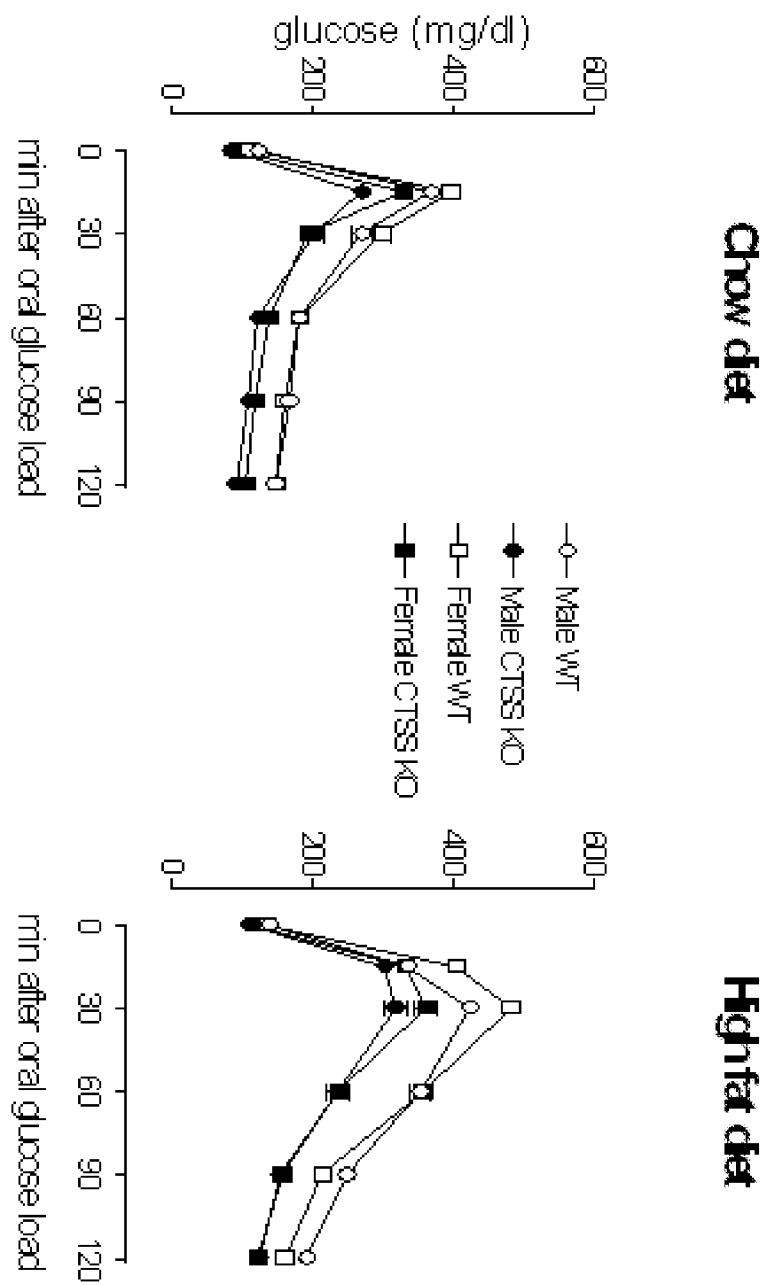

FIG. 6: The glycemic response to an oral glucose load is consistently lower in Cathepsin S deficient mice (CTSS KO) than in wild-type control mice, for mice of both sexes and whatever the diet. n=10 to 12 per group.

Figure 7:
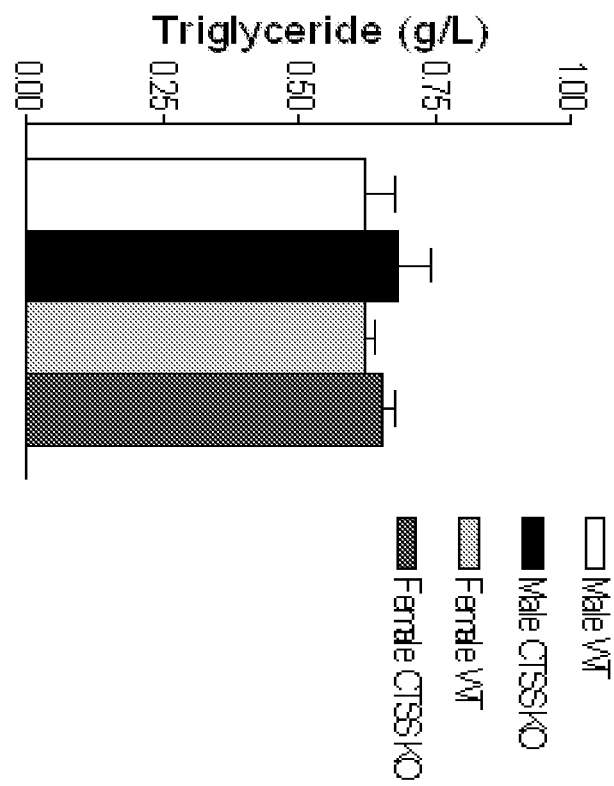
Figure 7:
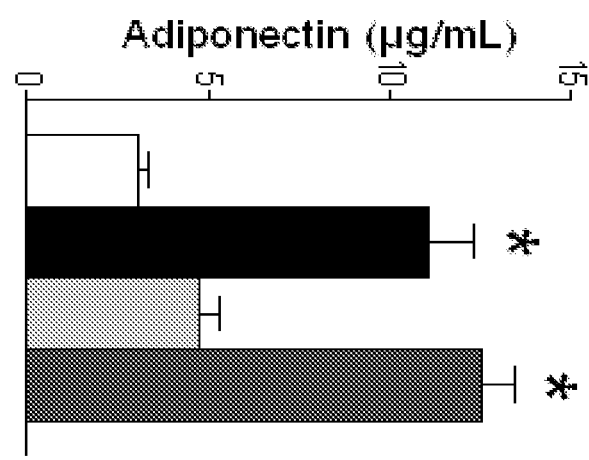

FIG. 7: Cathepsin S deficiency (CTSS KO) does not alter the level of triglycerides and markedly increased the circulating level of the insulin-sensitizing hormone adiponectin in male and female mice fed a high fat diet, as compared to wild-type control mice (WT). n=10 to 12 per group.

Figure 8:
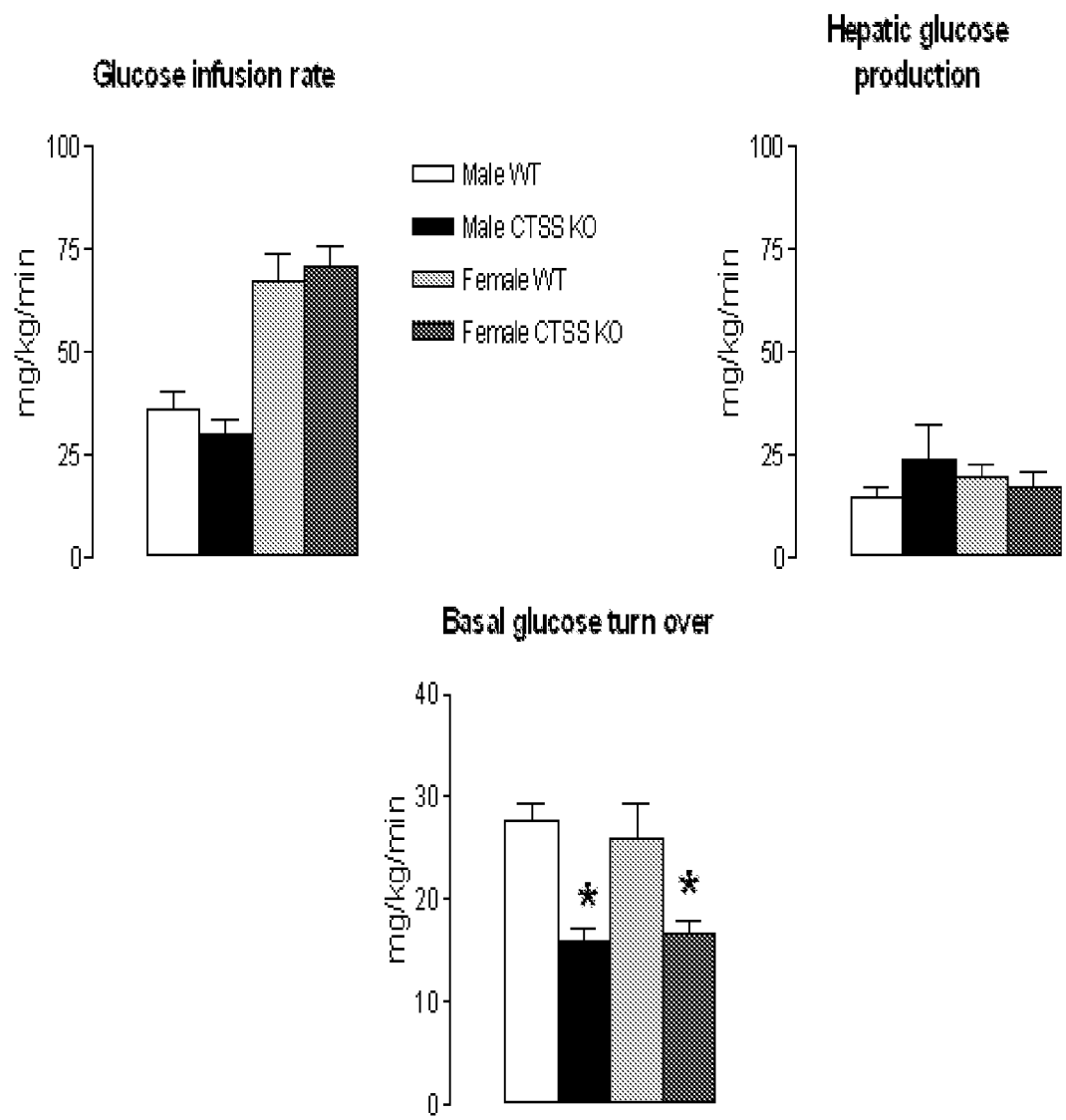

FIG. 8: The glucose infusion rate and hepatic glucose production during euglycemic-hyperinsulinemic clamp are similar in Cathepsin S deficient (CTSS KO) and wild-type control mice (WT) fed a high fat diet. n=5 to 7 per group. Basal glucose turn over rate is decreased in Cathepsin S deficient mice (CTSS KO) fed a high fat diet. n=4 to 6 per group FIG. 9: The level of expression of neoglucogenic (PEPCK, F1,6 BP, G6-Pase and PGC1 alpha) and lipogenic (ACC, FASN, PPARγ and SREBP1C) is similar in the liver of chow-fed wild-type (WT) and CTSS KO (KO mice) and markedly decreased in CTSS KO mice in response to a high fat diet. n=6-8 mice per group

EXAMPLES

Here, we present a series of data arising from human and mice studies, which show that inhibition of Cathepsin S could ameliorate glucose homeostasis in obese subjects.

Example 1

Material & Methods

1—Human Studies

The study enrolled a first population (P1) comprising 217 non diabetic obese subjects (BMI≥30 kg/m2) belonging to a larger population of individuals attending a metabolic ward at the Center for Detection and Prevention of Atherosclerosis (Marseille, France). The recruitment processes and study components have been previously described in (29). Local ethics committees approved the investigations and all subjects gave informed consent.

We also analyzed data obtained from a collaborative work of our team with Pr R. Rabasa-Lhoret, on a population of non-diabetic postmenopausal overweight and obese women. They were recruited from May 2003 to February 2006 for a weight-loss study by the Montreal Ottawa New Emerging Team (MONET) in the Department of Nutrition, Université de Montréal, Canada. Study inclusion and exclusion criteria were previously described in (30). The population (P2) included 137 women with mean age of 57.7±0.4 years and BMI 32.4±0.4 kg/m² who were weight-stable for 2 months prior to the study. All participants gave informed written consent before participation in accordance with the ethical guidelines of the Université of Montreal Research Ethics Committee. Among these subjects, 101 underwent a weight loss intervention for 6 months induced by a hypocaloric diet (1100 kcal to 1800 kcal with an energy deficit of 500 to 800 kcal/day). Subjects were submitted to an oral glucose tolerance test (OGTT) and to a hyperinsulinemic-euglycemic clamp (insulin infusion rate=75 mU/m²/min) for 180 min as previously described (30). Plasma glucose was measured in the basal state and 2 hrs after oral glucose load during OGTT. Whole body insulin sensitivity was evaluated by the quantitative insulin sensitivity check index (31): QUICKI=1/[log fasting insulin (μM)+log fasting glycemia (mg/dl)] and by the glucose infusion rate (mg/min/kg) normalized to fat free mass (MMT3) during the clamp.

2—Animal Studies

Animal Models

Various animal models were included in the study. To investigate the effect of obesity on Cathepsin S gene expression in adipose tissue, we used male obese Zucker rats, which bear a mutation (fa) in the leptin receptor gene, as compared to their lean counterpart. Second, we used a mice model of diet-induced obesity, produced by submitting wild-type male mice to a high fat diet, containing up to 72% of fat, for 8 to 12 weeks. Third, to assess the primary role of Cathepsin S in obesity and in glucose homeostasis, we used Cathepsin S deficient mice (CTSS KO), fed either a chow or a high fat diet. The CTSS KO mice were compared to aged-matched wild-type (WT) control mice of same gender.

Rodents were housed in a controlled environment, with free access to food and water. The animal experiments were validated by local ethical committees. Food intake was measured weekly during the experimental period by weighing the food container of cages housing 5 to 6 mice. Body weight was reported weekly. Various metabolic blood parameters were determined, including plasma glucose, triglyceride and adiponectin.

Oral Glucose Tolerance Test

An oral glucose tolerance test (OGTT) was performed. Mice were 6 hours fasted and glycaemia was assessed at the tail tip using a glucometer −30, 0, 15, 30, 60, 90 and 120 minutes after the oral glucose load.

Hyperinsulinemic-Euglycemic Clamp with 3H-Glucose

An intravenous catheter was implanted into the femoral vein under isoflurane anesthesia 5 to 6 days prior to the basal perfusions with 3H-glucose. The day of the clamp procedure, mice were fasted for 6 hours and insulin was infused at the rate of 4 mU/kg/min with 3H-glucose (30 μCi/min/kg) for 3 hours. Glucose (16.5%) was infused at variable rates in order to maintain euglycaemia. Blood was collected from the tip tail and biochemistry was performed in order to assess glucose specific activity and for calculation of the different parameters. In some experiments 3H-glucose (30 μCi/min/kg) was infused without insulin to determine "basal" glucose turn over.

3—Statistical Analyses

Data are expressed as mean±standard error of the mean (SEM). The Shapiro-Wilcoxon test was used to test the Gaussian distribution of clinical and biological measures. Skewed variables were log-transformed before statistical analyses. Student's t-test was used to assess for differences between groups. Associations between measures of serum Cathepsin S and covariates were assessed by Spearman's correlation coefficients (r). For adjustments, we used multiple linear regressions modelling using least squares means with Cathepsin S as the outcome variable. The results of the univariate correlation analyses were used as a guide for inclusion of covariates in the model. Statistical analysis was performed with JMP (SAS Institute Inc., Cary, N.C., USA). A p value≤0.05 was considered significant.

Results

1—Human Results

We have gathered experimental and clinical evidence suggesting that increased circulating Cathepsin S is associated with insulin resistance.

In P1 (217 non diabetic obese subjects), we found that Cathepsin S serum concentrations were positively correlated with fasting insulin (r=0.20, p=0.004) and negatively correlated with QUICKI (r=−0.20, p=0.003). These associations remain significant when adjusted for several parameters including age, gender, triglyceride and blood pressure (p<0.05).

In P2 (135 obese women), we analysed the association between circulating Cathepsin S and parameters of glucose metabolism in fasting state, in response to oral glucose load (OGTT) and during an euglycemic hyperinsulinemic clamp. Cathepsin S serum levels were positively correlated with plasma glucose in the basal state and at 2 hours after oral glucose administration (OGTT). A negative correlation was found with QUICKI and with MMT3 during the clamp procedure. Data are shown in the table below.

| Variables | Spearman's correlation coefficient (r) | P value |
| --- | --- | --- |
| Basal plasma glucose | 0.17 | <0.05 |
| 2 h plasma glucose | 0.21 | <0.05 |
| QUICKI | −0.19 | <0.05 |
| MMT3 | −0.19 | <0.05 |

In 101 women of P2 submitted to caloric restriction, Cathepsin S circulating levels were significantly reduced (8.8±2.2 vs 10.4±2.5 ng/ml p<0.0001), in line with our previous observations in an independent population of massively obese subjects submitted to by pass gastric surgery (32). Additionally, we observed an association between weight loss-induced reduction in serum Cathepsin S and amelioration of fasting glycemia (r=0.19, p=0.061), although the correlation did not reach statistical significance.

The association of serum Cathepsin S with parameters of glucose metabolism in humans is in line with the fact that in rodent models of insulin resistance induced by nutritional or genetic obesity, we systematically observed an increased expression of Cathepsin gene in the adipose tissue (FIG. 1).

2—Animal Results

Figure 2:
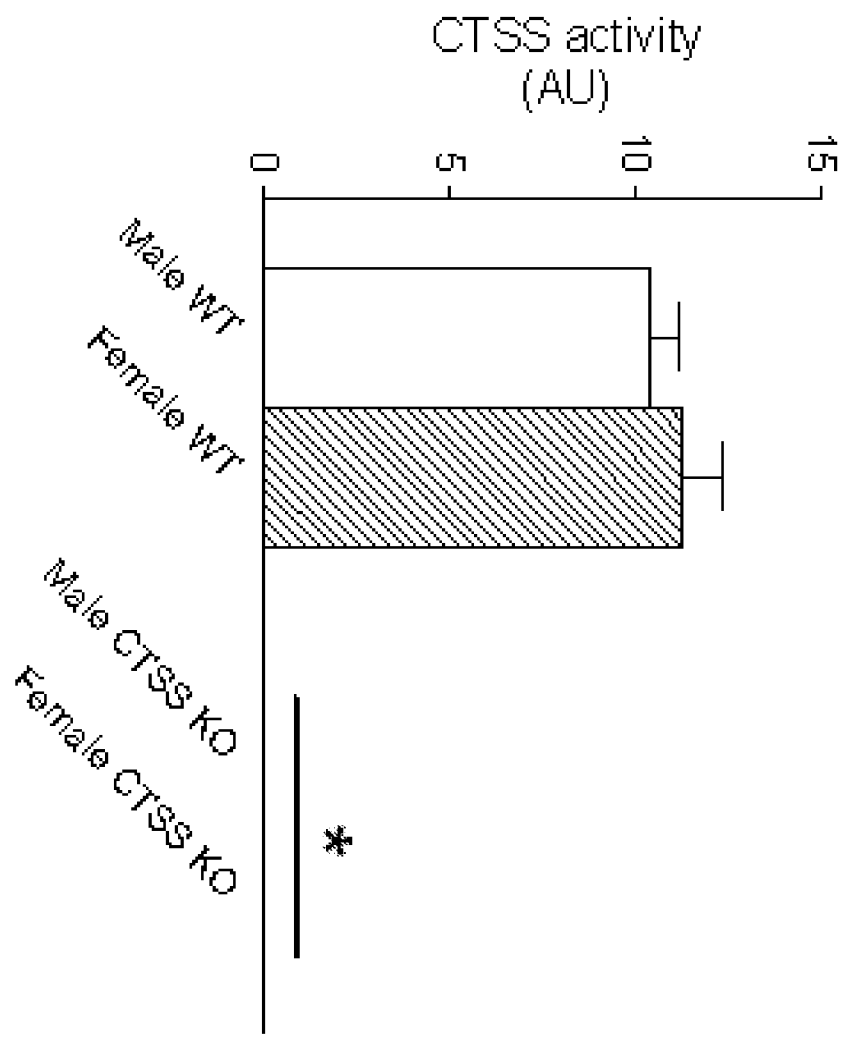

First, we validated the model of Cathepsin S deficient mice by measuring Cathepsin S activity in the spleen of WT and CTSS KO mice. We observed that the protease activity is indeed completely lost in the genetically modified mice, allowing us to continue the study (FIG. 2).

Both male and female CTSS KO mice were slightly heavier than WT controls and the difference due to genotype is greater under high fat diet than under chow diet (FIG. 3). Food intake was increased in CTSS KO male and female mice fed a normal diet, but was similar under high fat diet (FIG. 4).

Fasting blood glucose was significantly and consistently lower in CTSS KO mice (both male and female) than in age-matched WT mice (FIG. 5). This phenotype was observed in mice fed a chow diet and remained apparent under the high fat diet nutritional challenge. In addition, lower fasting glucose concentrations were observed in male CTSS KO aged 1 year as compared to aged and sex matched WT mice (CTSS KO: 0.74±0.072 n=3; WT: 1.10±0.047, n=4, p=0.007). This indicates that the phenotype of low plasma glucose associated with Cathepsin S deficiency persists during all life span.

In response to oral glucose administration, CTSS KO mice show a better glucose tolerance as illustrated in FIG. 6, where a lower pic of glycemia is observed in CTSS KO mice as compared to WT mice of both sexes. As expected, high fat diet deteriorates glucose tolerance in WT mice, as evidenced by higher glycemic excursion after glucose load. By contrast, CTSS KO mice remained strikingly normo-glucotolerant.

The absence of Cathepsin S did not significantly affect blood lipids, whatever the diet, as shown for triglycerides in FIG. 7. Unexpectedly, we observed that the circulating levels of adiponectin, an insulin-sensitizing hormone produced by the adipose cells, were markedly increased in CTSS KO male and female mice, as compared to WT mice (FIG. 7). Strikingly, this phenotype was observed in mice receiving a high fat diet, a nutritional challenge known to reduce adiponectin circulating levels in association with insulin resistance (33). Thus, this suggested to us that CTSS KO mice could display increased whole body insulin sensitivity, in line with amelioration of glucose tolerance shown by OGTT.

To test this hypothesis, CTSS KO mice were submitted to a euglycemic-hyperinsulinemic clamp. In this experimental setting, the glucose infusion rate is a measure of peripheral insulin sensitivity. These experiments were performed in mice fed a high fat diet to induce insulin resistance. Contrary to our hypothesis, CTSS KO mice did not display increased insulin sensitivity in these nutritional conditions, as shown by similar glucose infusion rate in CTSS KO and WT mice (male and female) (FIG. 8). In addition, we determined the rate of hepatic glucose production, which was also not statistically different in CTSS KO and WT mice. These results indicate that the deficiency of Cathepsin S does not alter peripheral and hepatic insulin sensitivity in mice. Glucose utilization was also determined in the absence of hyperinsulinemia (="basal"). In these experimental conditions, we observed that CTSS KO mice of both genders displayed decreased glucose turn over rate, suggesting that their hepatic glucose production is lower than in WT mice (FIG. 8).

These preliminary data indicate that Cathepsin S gene deletion slightly increases body-weight gain. Despite this effect on body weight, the absence of Cathepsin S affects whole body glucose homeostasis in a way that decreases blood glucose levels and ameliorate glucose tolerance. This phenotype is maintained when mice are submitted to a high fat nutritional challenge and in older mice. Absence of Cathepsin S does not alter whole body insulin sensitivity, but may reduce hepatic glucose production. This result is consistent with their phenotype showing reduced blood glucose levels as compared to WT mice. Thus, it is of importance to explore the cellular and molecular mechanisms leading to this beneficial phenotype and to determine if Cathepsin S inhibitors administered to mice fed a normal or a high fat diet can reproduce the phenotype induced by Cathepsin S deficiency under the same nutritional condition. Of note, increased hepatic glucose production is an early defect in the progression of type 2 diabetes. In this context, the potential negative control of hepatic glucose production through inhibition of Cathepsin S represents a promising new therapeutic approach to postpone the development of the disease.

Example 2

Changes in Energy Balance Predominantly Affect Cathepsin S in Adipose Tissue and in Circulation Materials and Methods Human Participants.

We recruited two clinical cohorts for this study. Firstly, from 2003 to 2006, 45 obese females were prospectively recruited from the gastric surgery program at the Department of Nutrition at Hôtel-Dieu Hospital (Paris, France). The women met the criteria for obesity surgery (i.e. BMI≥40 kg/m$^2$ or ≥35 kg/m$^2$ with at least one co-morbidity). They were excluded if they had evidence of inflammatory or infectious diseases, cancer, known alcohol consumption, as well as liver or kidney diseases. In this group, 7 women were classified as type 2 diabetic patients. Participants underwent a comprehensive clinical investigation before and 3 months after surgery, and were weight stable for 3 months before surgery. Seventeen normal weight and healthy female volunteers living in the same area as the obese subjects were recruited as a control group. This group of non-obese and obese women included is called Cohort 1. The Ethics Committee of the Hôtel-Dieu Hospital approved the investigations and all participants gave written informed consent.

The second group (Cohort 2) included 29 postmenopausal non-diabetic women. They were recruited in the Montreal area (Canada) from 2003 to 2006 for a 6 month medically supervised weight loss program. Weight fluctuation was less than 2 kg for one month before inclusion. A hypocaloric diet of 500-800 kcal/day deficit was designed by using the food exchange list of the Canadian Diabetes Association. The women were prescribed a balanced diet providing 1100 to 1800 kcal/day. Food was self-selected and the macronutrient composition was standardized under the supervision of a registered dietician. All participants gave informed written consent before participating in the study in accordance with the ethical guidelines of the Université de Montréal Research Ethics Committee.

Human Tissue Samples.

Biopsies of various human tissues were obtained during gastric by-pass surgery in cohort 1 obese subjects, including subcutaneous and omental adipose tissue, jejunum, as the distal part of the Roux-en-Y gastrojejunostomy (i.e. 40 cm distal to the Treitz angle), liver, from the left hepatic lobe, and abdominal external oblique muscle. Surgical subcutaneous adipose tissue biopsies were obtained in a separate group of 13 non obese female subjects (Age: 38.8±2.48 years; BMI: 22.3±0.64 kg/m$^2$) during elective surgery (plastic surgery of abdominal wall, hernia or hysterectomy). Tissue samples were stored at −80° C. until RNA extraction.

Adipose Tissue Cell Fractionation and Culture.

Adipocytes and cells of the stromal vascular fraction (SVF) were separated by collagenase digestion of adipose tissue when a sufficient amount (around 2 g) was obtained. Cells of the SVF were separated into endothelial cells (CD34$^+$/CD31$^+$) and macrophages (CD34$^-$/CD14$^+$) by immunoselection. Cells were lysed in RLT lysis buffer and stored at −20° C. until RNA extraction. Pre-adipocytes were isolated after 2 passages of total SVF cells and either directly lysed in RLT lysis buffer and stored at −20° C. before RNA extraction or differentiated for 10 days in the absence or presence of conditioned medium from human blood monocyte-derived macrophages. For the culture of adipose tissue explants, around 300 mg of thoroughly minced adipose tissue fragments (~4 to 8 mm$^3$) were incubated in 2 ml of ECBM (Promocell, Heidelberg, Germany) containing 3% bovine serum albumin and antibiotics for 24 hrs. Incubations were performed at least in triplicate. Conditioned media was stored at −80° C. until use.

Diet-Induced Obese Mice.

Starting at 6 weeks of age, eighteen C57/BL6NTAC male mice (Taconic Farms, Germantown, USA) were maintained on a high fat diet (60% calories from fat, n=9) or a chow diet (10% calories from fat, n=9) for 11 weeks. Mice were housed in a controlled environment with a 12 h light/dark cycle and free access to food and water. By the end of the feeding period, epididymal and inguinal adipose tissues were collected and stored −80° C. until RNA extraction. Protocols for animal use were reviewed and approved by the Animal Care Committee of the Joslin Diabetes Center and were in accordance with Institutional Animal Care and Use Committee guidelines.

RNA Preparation and Real Time PCR.

RNA extraction was performed using the RNeasy RNA Mini Kit (Qiagen, Courtaboeuf, France). Total RNA concentration and quality was confirmed using the Agilent 2100 bioanalyser (Agilent Technologies, Massy, France). Total RNA (1 μg) was reversed transcribed using random hexamers and Supercript II reverse transcriptase. Real time PCR was conducted using 25 ng cDNA with Taqman universal PCR mix in ABI 7700 (Applied Biosystems, Minneapolis, Minn., USA). mRNA values were normalized to 18S rRNA (Eurogentec, Angers, France). Primers for human and mouse cathepsins S, L and K genes are used.

Cathepsins, Cystatin C and Leptin Determination in Serum and Culture Medium.

Cathepsin concentrations were measured in the serum and in the culture media of adipose tissue explants by enzyme-linked immunosorbent assay (ELISA). Cathepsin S(R&D Systems, Oxford, UK), cathepsin L (Tebu Bio, Le Perray en Yvelines, France) and cathepsin K (Immunodiagnostic Systems, Paris, France) were determined as per the kit instructions. The limit of detection was as follows: cathepsin S: 0.02 ng/ml; cathepsin L: 1.71 ng/ml and cathepsin K: 1.1 pmol/l. The intra-assay variability was less than 9% and the inter-assay variability was less than 11% for each cathepsin. Cystatin C was measured by a particle-enhanced immunonephelometric assay (DakoCytomation, Trappes, France) on an Image analyser (Beckman-Coulter, Villepinte, France). The assay's analytical sensitivity was 0.07 μg/ml, and the intra- and inter-assay variability was 2.4% and 2.2%, respectively. The concentrations of leptin were determined in the same samples as cathepsins by ELISA (Quantikine human leptin, R&D Systems, Oxford, UK).

Statistical Analyses.

Data are expressed as mean±standard error of the mean (SEM). Not normally distributed data were log transformed. Student's t tests were used to assess group differences. Pearson's correlation coefficients were calculated to assess associations between serum cathepsins and biochemical variables or their variations with weight loss. We applied multiple linear regression modelling using adjustment for least squares means to address the influence of age and BMI on significant correlations. Statistical analyses were performed with JMP (SAS Institute Inc., Cary, USA) statistics software. A p value≤0.05 was considered significant.

Results

Cathepsins Gene Expression in Adipose Tissue and Adipose Tissue Cell-Types.

The three forms of cathepsins were highly expressed in human adipose tissue. High levels of cathepsin S were detected in the adipose, but also in jejunum, while high levels of cathepsins L and K were only detected in the adipose tissue, as compared to jejunum, liver and muscle of the same obese subject. Moreover, cathepsins S and L mRNA levels were 2-fold higher in omental than in subcutaneous adipose tissue.

Adipose tissue cell fractionation showed that cathepsins S, L and K were expressed in both adipocytes and cells of the SVF, with cathepsins S and K mRNA levels being higher in stromal cells than in adipocytes. Among SVF cells, macrophages had the highest levels of cathepsins S and L, while cathepsin K was equally expressed in endothelial cells, pre-adipocytes and macrophages.

Effect of Macrophage-Derived Factors on Cathepsin Gene Expression in Human Adipocytes.

To evaluate the effect of inflammatory factors on cathepsin gene expression, human primary pre-adipocytes were differentiated in presence of conditioned media of blood-derived macrophages activated or not with LPS. Cathepsin S mRNA level was 2-fold higher in the cells differentiated with the medium of LPS-activated macrophages, but cathepsin L and K gene expression remained unchanged. No significant change was found in adipose cells differentiated in non-activated macrophages medium.

Effect of Obesity on Cathepsin Gene Expression in Human and Rodent Adipose Tissue.

To evaluate the effect of obesity, we measured the respective mRNA level for each cathepsin in subcutaneous adipose tissue of obese and normal weight women. Cathepsin S gene expression was two-fold higher in adipose tissue of obese subjects compared to non obese controls. In contrast, we found no significant changes in cathepsin K and cathepsin L mRNA levels. However, in obese rodents, all three cathepsins were upregulated in adipose tissue, measured in the inguinal fat of mice fed a high fat diet. The three forms of cathepsin were also up-regulated in the epidydimal adipose tissue of these mice, as well as in inguinal and retroperitoneal fat of genetically obese Zucker rats. Thus, cathepsins S, L and K are increased in the adipose tissue of obese rodent, while only cathepsin S is significantly affected in human obesity.

Effect of Obesity on Cathepsins Release in Human Adipose Tissue Explants.

To further examine the effect of obesity on adipose tissue cathepsins, we measured their individual rate of release using subcutaneous adipose tissue explants obtained from obese and non obese individuals. In 24 hr conditioned media, cathepsins S and L were readily detectable, while cathepsin K concentration was below the detection threshold of the ELISA. The rate of cathepsin S release was significantly higher in obese (35±2.7 ng/g/24 hrs, n=10) than in non obese adipose tissue (23±2.6 ng/g/24 hrs, n=5, $p<0.05$). No difference was found for cathepsin L (obese: 16±1.9, non-obese: 14±3.5 ng/g/24 hrs, p=0.632). Leptin release was 4-fold higher in obese (18±3.3 ng/g/24 hrs) than in non-obese adipose tissue conditioned media (5±2.0 ng/g/24 hrs, $p<0.05$).

Effect of Obesity and Weight Reduction on Serum Cathepsins.

We assessed the effect of obesity and weight reduction on circulating levels of the three cathepsins in the same subject in two cohorts with distinct clinical characteristics. Serum cathepsin K was consistently below the threshold of detection. In cohort 1, serum cathepsin S was increased in obese subjects, but no difference was seen for cathepsin L. Obese women were re-investigated 3 months after gastric surgery. As expected, weight loss of 15% of the initial body weight was accompanied by a significant decrease in serum leptin and amelioration of insulin sensitivity evidenced by increased QUICKI values. At the same time, serum cathepsin S was significantly reduced (−26%). In contrast, serum cathepsin L was unaffected. Of note, excluding the 7 obese women with type-2 diabetes did not significantly change the data. Cohort 2 comprised obese women, who were older and exhibited a lower BMI than obese subjects of cohort 1. In this group, caloric restriction resulted in a 5% reduction of BMI, accompanied by a slight but significant decrease in circulating leptin concentrations and amelioration of glycemic parameters. Similar to the observations in cohort 1, serum cathepsin S was significantly reduced by 32% at the end of caloric restriction period, while no significant change was detected in serum cathepsin L.

Additionally, we measured serum concentration of cathepsins' inhibitor, cystatin C. Circulating cystatin C levels were significantly higher in the obese women of cohort 1 as compared to controls. In response to weight loss, cystatin C did not change significantly in obese subjects of cohort 1, but decreased slightly in cohort 2. In both groups, the ratio of cystatin C/cathepsin S circulating concentrations significantly increases after weight loss.

Of note, the reduction of cathepsin S circulating levels was of the same order of magnitude in cohort 1 as cohort 2, despite distinct protocols for weight reduction and markedly different decreases in obese women's BMI. Consequently, we found no significant relationship between changes in serum cathepsin S and changes in BMI in a correlation analysis including obese subjects from both cohorts (p=0.971, n=74). In the whole group of non-obese and obese subjects before weight reduction, we found a positive correlation between circulating levels of cathepsin S and plasma triglycerides (r=0.25, p=0.022, n=91), which remained significant after adjustment for age and BMI (p=0.045). However, the strength of this relationship was dampened after exclusion of type-2 diabetic patients (p=0.091, n=84). When the effect of weight reduction was tested, changes in serum cathepsin S were correlated with changes in triglycerides (r=0.28, p=0.017, n=74), even if diabetic patients were excluded (r=0.32, p=0.008, n=67). These correlations persisted after adjustment for age and BMI variation (p=0.020 in whole obese group; p=0.016 after exclusion of diabetic patients). By contrast, no relationship was found between serum cathepsin S and glycemia, insulinemia or QUICKI, or between their variations with weight reduction in the obese group.

Conclusion

In humans, cathepsin S is more influenced than cathepsins L and K by changes in energy balance in adipose tissue and circulation.

Example 3

Analyze of Gene Expression in the Liver of CTSS KO Mice

As a follow up of the observation that basal glucose turnover rate is decreased in CTSS KO mice (FIG. 8), we have engaged an investigation of hepatic gene expression to estimate the activity of gluconeogenesis. This metabolic pathway controls hepatic glucose production. We expected that the absence of cathepsin S would reduced the level of expression of the genes involved in this pathway, thereby accounting for reduced hepatic glucose production in CTSS KO mice. Additionally, we determined the level of expression of selected enzymes and transcription factors involved in lipogenesis, a metabolic pathway that promotes fatty liver under a high fat nutritional challenge.

Methods

The liver of CTSS KO and age-matched wild-type mice was sampled in mice fed a chow or a high-fat diet for 8 weeks. RNA extraction was performed using the RNeasy RNA Mini Kit (Qiagen, Courtaboeuf, France). Total RNA concentration and quality was confirmed using the Agilent 2100 bioanalyser (Agilent Technologies, Massy, France). Total RNA (1 µg) was reversed transcribed using random hexamers and Supercript II reverse transcriptase. Real time PCR was conducted using 25 ng cDNA with Taqman universal PCR mix in ABI 7700 (Applied Biosystems, Minneapolis, Minn., USA). mRNA values were normalized to 18S rRNA (Eurogentec, Angers, France). Appropriate primers were used to determine the level of expression of selected enzymes and transcription factors involved in gluconeogenesis (PEPCK, F1,6 BP, G-6-Pase, PGC1α) and lipogenesis (FAS, ACC, PPARγ, SREBP1C).

Results

In mice fed a normal chow diet, virtually all the genes investigated were expressed at a similar level in wild-type and CTSS KO mice, indicating that cathepsin S deletion is unlikely to markedly alter gluconeogenesis and lipogenesis in the liver. However, the response to a high fat diet, is substantially affected in the absence of cathepsin S. While this nutritional challenge tends to increase gluconeogenic and lipogenic genes in wild-type mice, as expected, there is a drastic reduction in the level of expression of these genes in CTSS KO mice (FIG. 9).

These data indicate that the lack of cathepsin S promotes a favourable liver phenotype with reduced glucose production and diminished steatosis despite increased fat mass under the high fat diet.

This suggests that inhibiting cathepsin S could be interesting in the management of hepatic diseases such as NAFLD and NASH, which are liver pathologies well-known to predispose to cirrhosis and increase cancer risk.

REFERENCES

Throughout this application, various references describe the state of the art to which this invention pertains. The disclosures of these references are hereby incorporated by reference into the present disclosure.

1. Scheen A J: New therapeutic approaches in type 2 diabetes. Acta Clin Belg 63:402-407, 2008
2. Semenkovich C F, Heinecke J W: The mystery of diabetes and atherosclerosis: time for a new plot. Diabetes 46:327-334, 1997
3. Yan L L, Daviglus M L, Liu K, Stamler J, Wang R, Pirzada A, Garside D B, Dyer A R, Van Horn L, Liao Y, Fries S F, Greenland P: Midlife body mass index and hospitalization and mortality in older age. Jama 295:190-198, 2006
4. Scheen A J: Antidiabetic agents in subjects with mild dysglycaemia: prevention or early treatment of type 2 diabetes? Diabetes Metab 33:3-12, 2007
5. Intensive blood-glucose control with sulphonylureas or insulin compared with conventional treatment and risk of complications in patients with type 2 diabetes (UKPDS 33). UK Prospective Diabetes Study (UKPDS) Group. Lancet 352:837-853, 1998
6. Effect of intensive blood-glucose control with metformin on complications in overweight patients with type 2 diabetes (UKPDS 34). UK Prospective Diabetes Study (UKPDS) Group. Lancet 352:854-865, 1998
7. Kahn S E, Haffner S M, Heise M A, Herman W H, Holman R R, Jones N P, Kravitz B G, Lachin J M, O'Neill M C, Zinman B, Viberti G: Glycemic durability of rosiglitazone, metformin, or glyburide monotherapy. N Engl J Med 355: 2427-2443, 2006
8. Turk V, Turk B, Turk D: Lysosomal cysteine proteases: facts and opportunities. EMBO J. 20:4629-4633, 2001
9. Taleb S, Lacasa D, Bastard J P, Poitou C, Cancello R, Pelloux V, Viguerie N, Benis A, Zucker J D, Bouillot J L, Coussieu C, Basdevant A, Langin D, Clement K: Cathepsin S, a novel biomarker of adiposity: relevance to atherogenesis. FASEB J. 19:1540-1542, 2005
10. Yang M, Zhang Y, Pan J, Sun J, Liu J, Libby P, Sukhova G K, Doria A, Katunuma N, Peroni O D, Guerre-Millo M, Kahn B B, Clement K, Shi G P: Cathepsin L activity controls adipogenesis and glucose tolerance. Nat. Cell Biol 9:970-977, 2007
11. Taleb S, Cancello R, Clement K, Lacasa D: Cathepsin s promotes human preadipocyte differentiation: possible involvement of fibronectin degradation. Endocrinology. 147:4950-4959, 2006
12. Funicello M, Novelli M, Ragni M, Vottari T, Cocuzza C, Soriano-Lopez J, Chiellini C, Boschi F, Marzola P, Masiello P, Saftig P, Santini F, St Jacques R, Desmarais S, Morin N, Mancini J, Percival M D, Pinchera A, Maffei M: Cathepsin K null mice show reduced adiposity during the rapid accumulation of fat stores. PLoS. ONE. 2:e683, 2007
13. Lecaille F, Kaleta J, Bromme D: Human and parasitic papain-like cysteine proteases: their role in physiology and pathology and recent developments in inhibitor design. Chem Rev 102:4459-4488, 2002
14. Markt P, McGoohan C, Walker B, Kirchmair J, Feldmann C, De Martino G, Spitzer G, Distinto S, Schuster D, Wolber G, Laggner C, Langer T: Discovery of novel cathepsin S inhibitors by pharmacophore-based virtual high-throughput screening. J Chem Inf Model 48:1693-1705, 2008
15. Irie O, Ehara T, Iwasaki A, Yokokawa F, Sakaki J, Hirao H, Kanazawa T, Teno N, Horiuchi M, Umemura I, Gunji H, Masuya K, Hitomi Y, Iwasaki G, Nonomura K, Tanabe K, Fukaya H, Kosaka T, Snell C R, Hallett A: Discovery of selective and nonpeptidic cathepsin S inhibitors. Bioorg Med Chem Lett 18:3959-3962, 2008
16. Kohler G, Milstein C: Continuous cultures of fused cells secreting antibody of predefined specificity. Nature 256: 495-497, 1975
17. Cote R J, Morrissey D M, Houghton A N, Beattie E J, Jr., Oettgen H F, Old L J: Generation of human monoclonal antibodies reactive with cellular antigens. Proc Natl Acad Sci USA 80:2026-2030, 1983
18. Tuerk C, Gold L: Systematic evolution of ligands by exponential enrichment: RNA ligands to bacteriophage T4 DNA polymerase. Science 249:505-510, 1990
19. Jayasena S D: Aptamers: an emerging class of molecules that rival antibodies in diagnostics. Clin Chem 45:1628-1650, 1999
20. Colas P, Cohen B, Jessen T, Grishina I, McCoy J, Brent R: Genetic selection of peptide aptamers that recognize and inhibit cyclin-dependent kinase 2. Nature 380:548-550, 1996
21. Elbashir S M, Harborth J, Lendeckel W, Yalcin A, Weber K, Tuschl T: Duplexes of 21-nucleotide RNAs mediate RNA interference in cultured mammalian cells. Nature 411:494-498, 2001
22. Tuschl T, Zamore P D, Lehmann R, Bartel D P, Sharp P A: Targeted mRNA degradation by double-stranded RNA in vitro. Genes Dev 13:3191-3197, 1999
23. Hannon G J: RNA interference. Nature 418:244-251, 2002
24. Brummelkamp T R, Bernards R, Agami R: A system for stable expression of short interfering RNAs in mammalian cells. Science 296:550-553, 2002
25. McManus M T, Haines B B, Dillon C P, Whitehurst C E, van Parijs L, Chen J, Sharp P A: Small interfering RNA-mediated gene silencing in T lymphocytes. J Immunol 169:5754-5760, 2002
26. Wu Z, Asokan A, Samulski R J: Adeno-associated virus serotypes: vector toolkit for human gene therapy. Mol Ther 14:316-327, 2006
27. Choi V W, Samulski R J, McCarty D M: Effects of adeno-associated virus DNA hairpin structure on recombination. J Virol 79:6801-6807, 2005
28. Hoheisel J D: Microarray technology: beyond transcript profiling and genotype analysis. Nat Rev Genet. 7:200-210, 2006
29. Juhan-Vague I, Renucci J F, Grimaux M, Morange P E, Gouvernet J, Gourmelin Y, Alessi M C: Thrombin-activatable fibrinolysis inhibitor antigen levels and cardiovascular risk factors. Arterioscler. Thromb. Vasc. Biol. 20:2156-2161, 2000
30. Bastard J P, Vandernotte J M, Faraj M, Karelis A D, Messier L, Malita F M, Garrel D, Prud'homme D, Rabasa-Lhoret R: Relationship between the hyperinsulinemic-euglycaemic clamp and a new simple index assessing insulin sensitivity in overweight and obese postmenopausal women. Diabetes Metab 33:261-268, 2007
31. Katz A, Nambi S S, Mather K, Baron A D, Follmann D A, Sullivan G, Quon M J: Quantitative insulin sensitivity check index: a simple, accurate method for assessing insulin sensitivity in humans. J. Clin. Endocrinol. Metab 85:2402-2410, 2000

32. Taleb S, Cancello R, Poitou C, Rouault C, Sellam P, Levy P, Bouillot J L, Coussieu C, Basdevant A, Guerre-Millo M, Lacasa D, Clement K: Weight loss reduces adipose tissue cathepsin S and its circulating levels in morbidly obese women. J. Clin. Endocrinol Metab. 91:1042-1047, 2006

33. Guerre-Millo M: Adiponectin: an update. Diabetes Metab 34:12-18, 2008

34. Cole et al. "Monoclonal Antibodies and Cancer Therapy", Alan R. Liss, Inc., 1985, pp. 77-96.

35. Murry, "Methods in Molecular Biology," vol. 7, Humana Press, Inc., Cliffton, N.J., 1991.

36. Sambrook J, Fritsch E F, Maniatis T. Molecular cloning: a laboratory manual, 2nd edition. Cold Spring Harbor Laboratory Press, Cold Spring Harbor, N.Y. 1989.

37. Gauthier J Y, Cameron Black W, Courchesne I, Cromlish W, Desmarais S, Houle R, Lamontagne S, Chun Sing Li, Massé F, McKay D J, Ouellet M, Robichaud J, Truchon J F, Truong V L, Wang O and Percival D. The identification of potent, selective, and bioavailable cathepsin S inhibitors. Bioorganic & Medicinal Chemistry Letters 17 (2007) 4929-4933.

38. Shindo K, Suzuki H, Okuda T. Paecilopeptin, a new cathepsin S inhibitor produced by Paecilomyces carneus. Bioscience, biotechnology, and biochemistry. 2002, vol. 66, no 11, pp. 2444-2448

The invention claimed is:

1. A method for reducing glucose production in a subject in need thereof to prevent obesity-associated disorders selected from the group consisting of type 2 diabetes, hyperglycemia, glucose intolerance or dyslipidemia, insulin resistance, hyperinsulinemia, and hepatic disease, comprising the step of administering to said subject an effective amount of an inhibitor of Cathepsin S, wherein said inhibitor of Cathepsin S is selected from paecilopeptin, 4-morpholineurea-Leu-HomoPhe-vinylsulfone, and

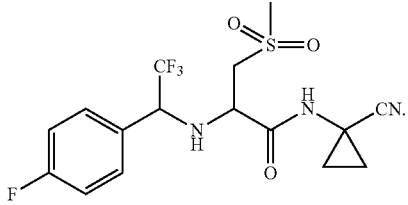 [SMILES: CS(=O)(=O)CC(NC(c1ccc(F)cc1)C(F)(F)F)C(=O)NC1(C#N)CC1]

* * * * *